(12) United States Patent
Mauborgne et al.

(10) Patent No.: US 10,852,283 B2
(45) Date of Patent: Dec. 1, 2020

(54) SYSTEMS AND METHODS FOR DETECTING A NEUTRON GENERATOR OPERATING IN AIR

(71) Applicant: Schlumberger Technology Corporation, Sugar Land, TX (US)

(72) Inventors: Marie-Laure Mauborgne, Sugar Land, TX (US); Francoise Allioli, Clamart (FR); Mauro Manclossi, Clamart (FR); Luisa Nicoletti, Clamart (FR)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 428 days.

(21) Appl. No.: 15/841,641

(22) Filed: Dec. 14, 2017

(65) Prior Publication Data

US 2019/0187116 A1    Jun. 20, 2019

(51) Int. Cl.
*G01N 33/00* (2006.01)
*G01V 5/10* (2006.01)

(52) U.S. Cl.
CPC ..... *G01N 33/0073* (2013.01); *G01N 33/0027* (2013.01); *G01V 5/108* (2013.01)

(58) Field of Classification Search
CPC .......... G01N 33/0027; G01N 33/0073; G01V 5/102; G01V 5/108
See application file for complete search history.

(56) References Cited

U.S. PATENT DOCUMENTS

| 6,207,953 B1 * | 3/2001 | Wilson | G01V 5/104 250/269.4 |
| 6,649,906 B2 | 11/2003 | Adolph et al. | |
| 2014/0001350 A1 * | 1/2014 | Beekman | G01V 5/125 250/269.6 |

* cited by examiner

*Primary Examiner* — Mark R Gaworecki

(57) ABSTRACT

A system that may identify when a pulsed neutron generator is operating while disposed in an undesirable environment, such as in air, may include a pulsed neutron generator designed to emit neutrons in an environment. The system may also include a radiation detector designed to take measurements of the neutrons. The system may also include data processing circuitry designed to determine if the environment surrounding the pulsed neutron generator is air based at least in part on a neutron signal obtained by the radiation detector. The determination may include comparing one or more characteristics of the neutron signal with corresponding reference characteristics.

19 Claims, 11 Drawing Sheets

SYSTEMS AND METHODS FOR DETECTING A NEUTRON GENERATOR OPERATING IN AIR

BACKGROUND

This disclosure relates to using pulsed neutron generator based measurements to determine the environment around a tool for use downhole. Such measurements may be used to deactivate neutron emission from the pulsed neutron generator based on the determined environment.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Producing hydrocarbons from a borehole drilled into a geological formation is a remarkably complex endeavor. In many cases, decisions involved in hydrocarbon exploration and production may be informed by measurements from downhole well-logging tools that are conveyed deep into the borehole. The measurements may be used to infer properties and characteristics of the geological formation surrounding the borehole. The discovery and observation of resources using downhole techniques generally takes place down in the borehole with sensors. These sensors may be a part of a tool-string that may be attached to a drill string or other downhole device.

In some instances, downhole tools may use an electronically-driven neutron source (e.g., a pulsed neutron generator (PNG)) along with one or more sensors to take measurements. The measurements may be used to estimate properties of the geological formation such as porosity, density, the yields of resources of interest in the area, and/or other desired characteristics. In general, high-energy neutrons may be emitted into the environment (e.g., the borehole and/or the geological formation). The high-energy neutrons may collide with, be captured by, and/or scatter off the nuclei of elements in the environment. Some of these interactions may cause the elements to emit gamma-rays having energies that vary depending on the type of element that emitted the gamma-ray. Multiple sensors (e.g., gamma-ray sensors, neutron sensors, etc.) may be utilized to then detect the gamma-rays and/or emitted neutrons. By analyzing the count rate, energy spectrum, or time spectrum of the gamma-rays and/or the count rate, energy spectrum, or time spectrum of the neutrons, properties of the environment may be determined. These measurements are generally obtained downhole, meaning that the downhole tool is operated while it is disposed in the borehole, not while the downhole tool is located at the surface.

One feature of neutron generators compared to radioisotopic neutron sources is that the generator can be turned off. This may prevent neutron emission before the tool is lowered into a wellbore, when it is removed from the wellbore, as well as during tests and calibrations in the shop. In such environments, a neutron detector may record a signal of neutrons having an energy above a threshold. If so, this may indicate that the downhole tool may be in air. Thus, in response to detecting this recorded signal, the downhole tool may be shut down.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

To better determine the environment around a tool utilizing a neutron source, neutron and/or neutron-induced gamma ray measurements may be used. Such measurements may also be used to deactivate neutron emission based on the determined environment. By way of example, this may allow a neutron source to be switched off when the environment includes significant presence of air, since the presence of air may indicate that the downhole tool is located at the surface and is not properly shielded rather than downhole.

Indeed, in one example, a system may include a pulsed neutron generator designed to emit neutrons in an environment. The system may also include a neutron and/or a gamma ray detector designed to take measurements of the neutrons or the neutron induced gamma rays respectively. The system may also include data processing circuitry designed to determine if the environment surrounding the pulsed neutron generator is air based at least in part on a time spectrum. Such a time spectrum may record the number of neutrons or gamma rays detected as a function of time with respect to the pulsing of the neutron generator.

In another embodiment, a method for automatically deactivating a neutron generator in an undesired environment may include emitting neutrons from the neutron generator into an environment. The method may also include detecting the neutrons or neutron induced gamma rays using one or more detectors and determining, via a processor, from the detected neutrons or gamma rays a time spectrum of a detected neutron or gamma ray count rate. The method may also include determining, via the processor, if the environment is undesirable based at least in part on one or more characteristics of the time spectrum, and, if the environment is undesirable, automatically disabling the neutron generator.

In another embodiment, machine-executable instructions stored on a tangible, non-transitory machine-readable storage medium, which, when executed by a machine, may cause the machine to perform a method according to the disclosure. The method may for instance include controlling an emission of neutrons from a neutron generator and processing signals received from one or more neutron and/or gamma ray sensors. The signals may be representative of neutrons or neutron induced gamma rays. The method may also include calculating a count rate spectrum over time based at least in part on the measurements and evaluating a difference between the count rate spectrum and a reference count rate spectrum. The method may also include determining if the neutron generator is in an air environment.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

Figure 1:
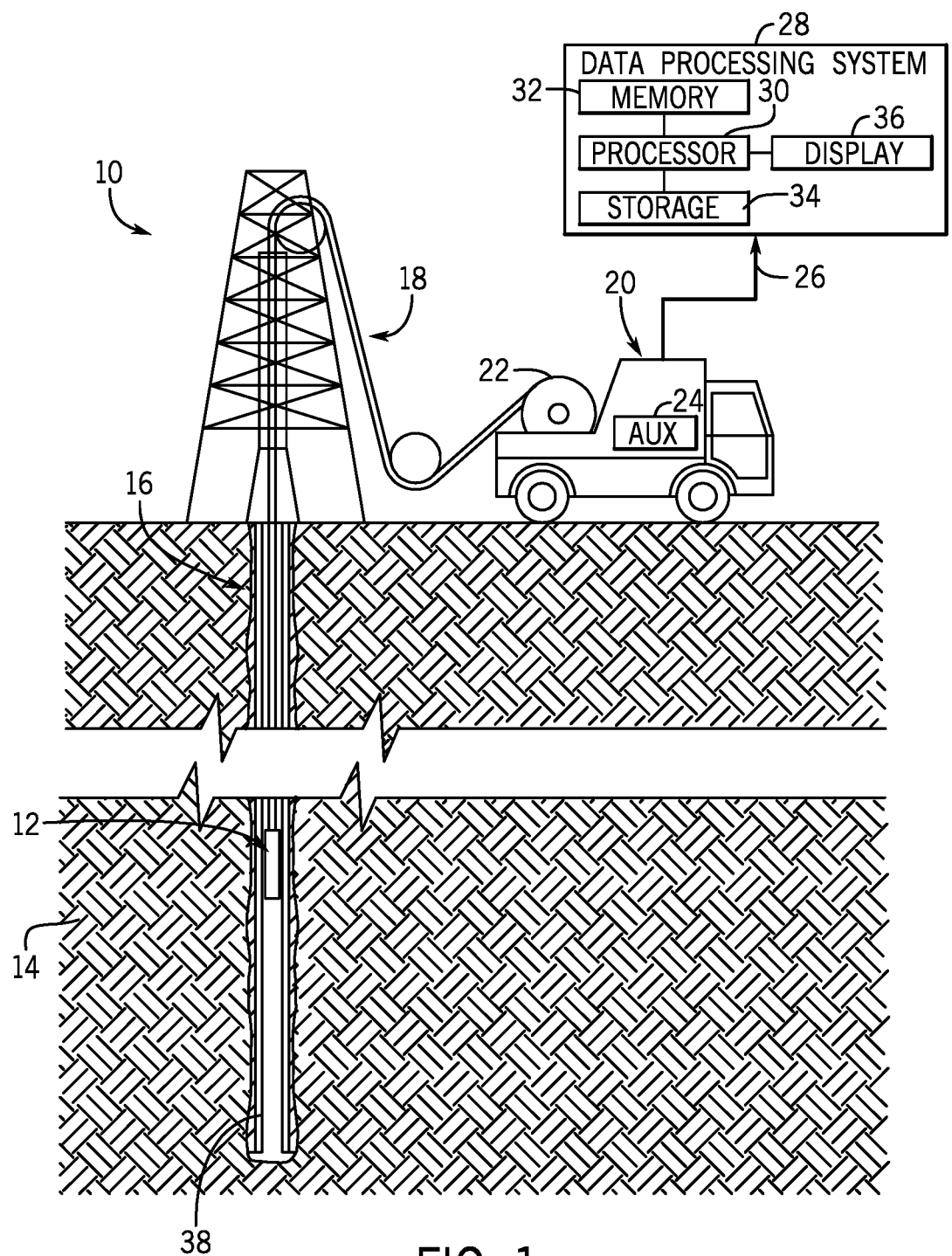
FIG. 1 is an example of a neutron-induced measurement system, in accordance with an embodiment.

One or more specific embodiments of the present disclosure will be described below. These described embodiments are examples of the presently disclosed techniques. Additionally, in an effort to provide a concise description of these embodiments, the features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

The oil and gas industry includes a number of sub-industries, such as experimentation, exploration, drilling, logging, extraction, transportation, refinement, retail, and so forth. During exploration, and drilling, boreholes may be drilled into the ground for reasons that may include discovery, observation, or extraction of resources. These resources may include oil, gas, water, or any other combination of elements within the ground.

Boreholes, sometimes called wellbores, may be straight or curved holes drilled into the ground from which resources may be discovered, observed, or extracted. During and/or after the establishment of a borehole, well logging may be practiced. Well logging may include making a detailed record of the geological formations penetrated by a borehole, and is generally part of the discovery and observation of resources.

The exploration of what lies beneath the ground may be accomplished by a number of methods including surface and downhole techniques. The discovery and observation of resources using downhole techniques generally takes place down in the borehole with sensors. These sensors may be a part of a tool-string that may be attached to a drill string or other downhole device.

In many implementations, downhole tools may include a neutron source to impart high-energy neutrons into the environment (e.g., borehole, geological formation, or other surroundings of the tool). The high energy neutrons may scatter inelastically or elastically off nuclei in the materials surrounding the downhole tool. Some inelastic scattering may result in the emission of gamma rays. Neutrons may slow down through elastic or inelastic scattering and may reach epithermal or thermal energy and eventually be captured by nuclei in the materials surrounding the tool. The neutron capture may result in the emission of gamma rays, the energies of which may vary depending on the type of element that emitted the gamma ray. These gamma-rays may then be detected by one or more detectors. Additionally, the emitted neutrons may bounce back from the environment and be detected by one or more neutron detectors. These gamma-ray and/or neutron detections may then be analyzed to determine characteristics of the environment. Additionally, the delay between neutron emission from the generator and neutron and/or gamma ray detection by the detector may be affected by the properties of the environment, such as density, porosity, and/or lithology.

Although the neutron source of a downhole tool may be activated regularly while down in the borehole, it may be undesirable to activate the neutron source in other environments, such as when the downhole tool is not down in a borehole or a controlled setting (e.g., laboratory, shop facility, or at the borehole, but not downhole). For example, if the downhole tool is in an environment of air, it may be desired to have the downhole tool automatically turn off and/or disable neutron emission. This may occur when a downhole tool has been activated before entering a borehole or is still active upon exiting the borehole. This may also occur, for example, in a laboratory or shop setting, when shielding (e.g., a water tank in which the tool is placed for metrology purposes such as calibrations and functional tests) is not present (e.g., the water has leaked out). In particular conditions, in addition to or instead of automatically disabling neutron emission, a notification may be sent to a user of the downhole tool.

In some embodiments, a downhole tool may detect neutrons and/or gamma-rays induced by the neutron emission to determine the surrounding environment. For example, a gamma-ray detector spaced at a distance from the neutron source, at which under downhole conditions no gamma rays or very few gamma rays are detected, along with a processor, may detect whether the gamma ray count rate above a high energy threshold is above a certain limit. If it is, this may indicate that the downhole tool may be in air. Thus, in response to detecting that the gamma-ray signal is above the threshold, the downhole tool may be shut down. However, this measurement by gamma-rays may be unreliable at times, as there may be an excessive gamma ray signal in boreholes filled with air or gas. As such, this may lead to an undesired shut down of the neutron generator.

Therefore, in one embodiment of the disclosure, a downhole tool may detect the environment around it by analyzing the counts of neutrons detected by a neutron sensor or a gamma ray detector positioned closer to the neutron source and intended to measure scattered neutrons or neutron induced gamma rays and determine if the environment is undesirable for neutron emission based at least in part on the detected signal. For example, signals corresponding to the neutron/gamma-ray detections may have particular characteristics (e.g., slopes, areas, peaks, etc. of time, energy, or other spectra). These signals may be compared to one or more reference characteristics. Such reference characteristics may include characteristics of a reference signal from a known environment which may be desirable or undesirable. Reference characteristics may also be set or variable values (e.g., a threshold value) corresponding to the characteristics of the detected signal. Additionally, signals based on gamma-ray detections may be corrected for background (e.g., natural) gamma-rays. Based on the comparison, the current environment may be estimated and determined to be desirable or undesirable. Such a detector may also be a detector that can detect both neutrons and gamma rays, such as a scintillation detector using a Li-glass, $Cs_2LiYCl_6$:Ce (CLYC) or NaIL™ (NaI(Tl), Li) scintillator for example.

With the foregoing in mind, FIG. 1 illustrates a well-logging system 10 that may employ the systems and methods of this disclosure. The well-logging system 10 may be used to convey a downhole tool 12 through a geological formation 14 via a borehole 16. In the example of FIG. 1, the downhole tool 12 is conveyed on a cable 18 via a logging winch system (e.g., vehicle) 20. Although the logging winch system 20 is schematically shown in FIG. 1 as a mobile logging winch system carried by a truck, the logging winch system 20 may be substantially fixed (e.g., a long-term installation that is substantially permanent or modular). Any suitable cable 18 for well logging may be used. The cable 18 may be spooled and unspooled on a drum 22 and an auxiliary power source 24 may provide energy to the logging winch system 20 and/or the downhole tool 12.

Moreover, while the downhole tool 12 is described as a wireline downhole tool, it should be appreciated that any suitable conveyance may be used. For example, the downhole tool 12 may instead be conveyed as a logging-while-drilling (LWD) tool as part of a bottom-hole assembly (BHA) of a drill string, conveyed on a slickline or via coiled tubing, and so forth. For the purposes of this disclosure, the downhole tool 12 may be any suitable downhole tool that uses neutron and or neutron-induced gamma ray measurements within the borehole 16 (e.g., downhole environment).

The downhole tool 12 may receive energy from an electrical energy device or an electrical energy storage device, such as the auxiliary power source 24 or another electrical energy source to power the tool. Additionally, in some embodiments the downhole tool 12 may include a power source within the downhole tool 12, such as a battery system or a capacitor to store sufficient electrical energy to activate the neutron source and record gamma-ray or neutron radiation.

Control signals 26 may be transmitted from a data processing system 28 to the downhole tool 12, and data signals 26 related to the downhole tool 12 measurements, such as the time spectra, may be returned to the data processing system 28 from the downhole tool 12. The data processing system 28 may be any electronic data processing system that can be used to carry out the systems and methods of this disclosure. For example, the data processing system 28 may include a processor 30, which may execute instructions stored in memory 32 and/or storage 34. As such, the memory 32 and/or the storage 34 of the data processing system 28 may be any suitable article of manufacture that can store the instructions. The memory 32 and/or the storage 34 may be read-only memory (ROM), random-access memory (RAM), flash memory, an optical storage medium, or a hard disk drive, to name a few examples. A display 36, which may be any suitable electronic display, may display images generated by the processor 30. The data processing system 28 may be a local component of the well-logging system 10 (e.g., incorporated with the logging winch system 20, the downhole tool 12, the downhole tool string, the bottom-hole assembly, etc.). Additionally, the data processing system 28 may be a remote device that analyzes data from other logging winch systems 20, a device located proximate to the drilling operation, or a combination thereof. In some embodiments, the data processing system 28 may be a mobile computing device (e.g., tablet, smart phone, or laptop) or a server remote from the logging winch system 20. The downhole tool 12 may be used in a borehole 16 with or without a casing 38, which may include pipe, cement, or other materials.

Figure 2:
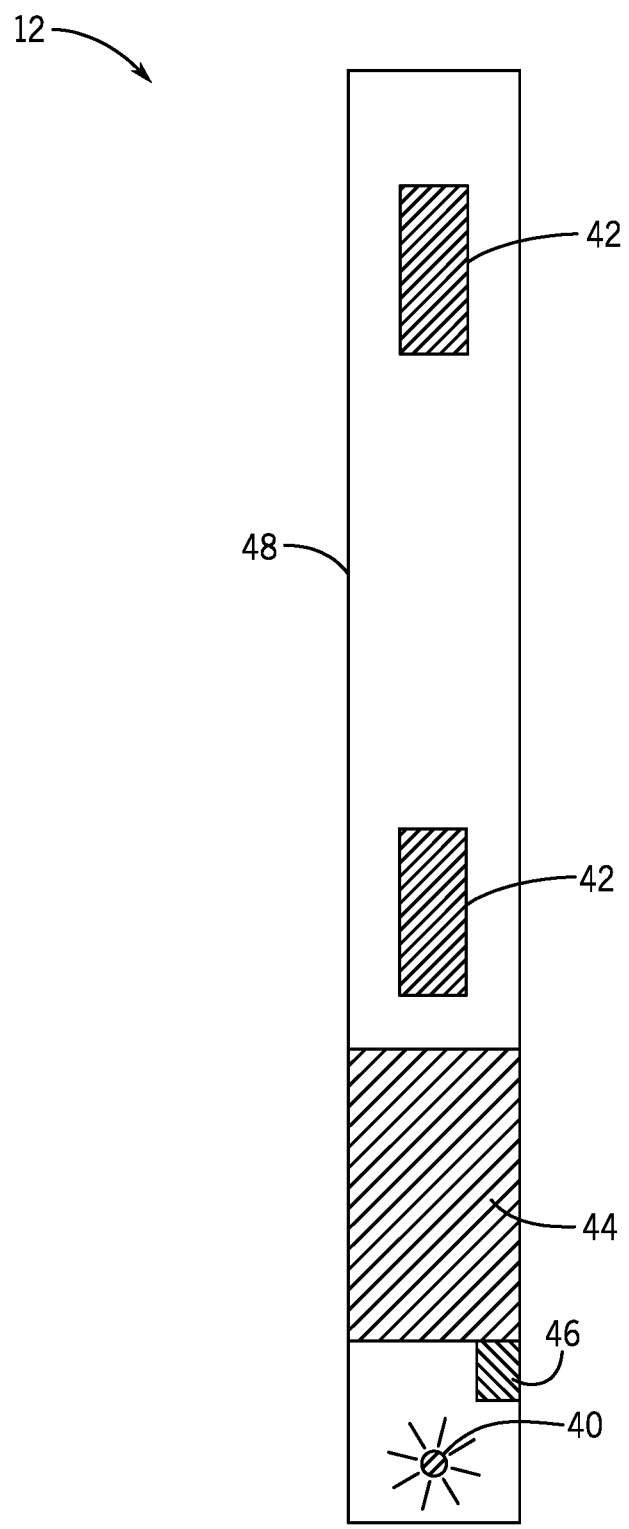
FIG. 2 is an example of a neutron-induced measurement downhole tool, in accordance with an embodiment.

As depicted in FIG. 2, the downhole tool 12 may include a neutron source 40 and one or more neutron and/or gamma ray detectors 42 (e.g., gas proportional detectors, scintillation neutron or gamma ray detectors, etc.). The detectors 42 may include gain-stabilized detectors, non-gain-stabilized detectors, or a combination thereof. Additionally, the neutron source 40 and detector(s) 42 may be separated by a neutron/gamma-ray shield 44. The shield 44 may prevent or reduce emitted neutrons or gamma rays from directly affecting the detectors 42 or minimize oversaturation. In some embodiments, a neutron monitor 46 may be implemented near the neutron source 40 to measure the output neutron flux of the neutron source 40. Additionally or alternatively, the neutron output of the neutron source 40 may be determined based on operating parameters of the neutron source 40 such as voltage, beam current, temperature, and/or calibration. In one embodiment, the neutron source 40, detector(s) 42, neutron monitor 46, and shield 44 are enclosed in a housing 48; however, the components may also be employed in separate housings. The neutron source 40 may be any suitable type of neutron generator (e.g., pulsed neutron generator (PNG)) that produces pulsed neutrons of sufficiently high energy for the desired function. When placed into the borehole 16 and activated, the neutron source 40 may emit high-energy neutrons into the surrounding formation 14 in multiple directions. These high-energy neutrons may interact with nuclei in the surrounding area in events including inelastic scattering, elastic scattering, and neutron capture, and may generate secondary (neutron-induced) gamma rays as a consequence of inelastic scattering or neutron capture. Neutrons may also be scattered back and detected by a neutron detector 42. Alternatively or additionally, gamma rays may be detected by a gamma ray detector 42.

Figure 3:
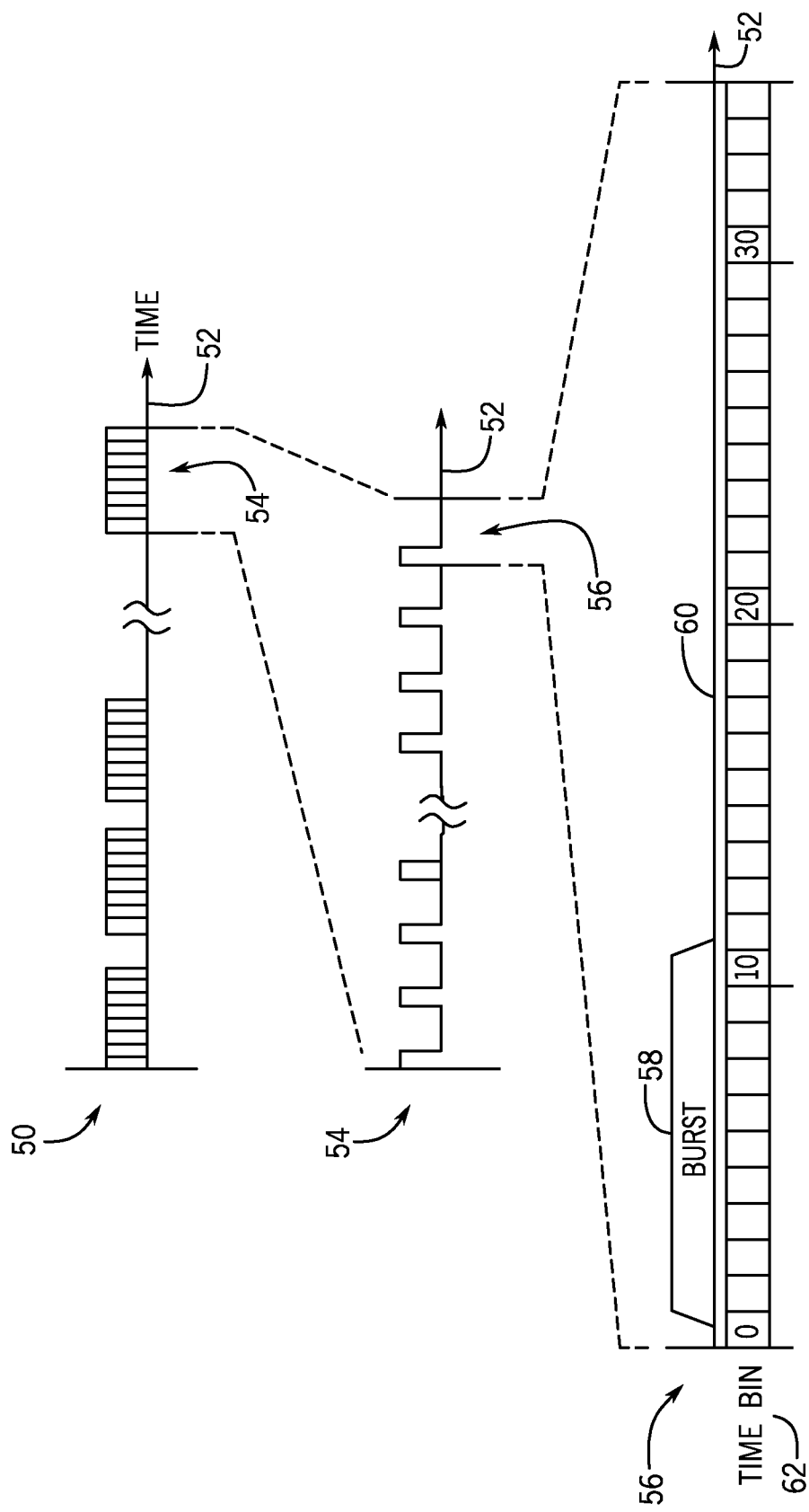
FIG. 3 is a plot of a neutron emission pulse sequence, in accordance with an embodiment.

The neutron source 40 may emit the high-energy neutrons in a pulsing scheme 50. FIG. 3 illustrates one embodiment of a pulsing scheme 50 with respect to time 52. A pulsing scheme 50 may include one or more packets 54. Packets 54 may include one or more pulses 56. In turn, the pulses 56 may include a neutron burst 58 and an "off" period 60. The neutron burst 58 may represent an "on" period of the neutron source 40 indicating a period of high-energy neutron emission. As such, the off period 60 may be a period of no or limited neutron emission between neutron bursts 58. In the illustrated embodiment, the pulse 56 may be broken down into time bins 62. Each time bin 62 may be used to illustrate a period in time 52 and may be any suitable arbitrary length. In one embodiment, each time bin 62 may correspond to 1 microsecond (μs). Additionally, the time 52 between pulses 56 and packets 54 may vary depending on the implementation of the downhole tool 12. The pulsing scheme 50 may also be set to separate the different types of interactions between neutrons and the nuclei in the material surrounding the downhole tool (e.g., elastic collisions, gamma rays induced by capture, gamma rays induced by inelastic collisions, etc.). Different pulsing schemes 50 may be used and/or adjusted to enhance the differentiation of one or more of these phenomena.

Figure 4:
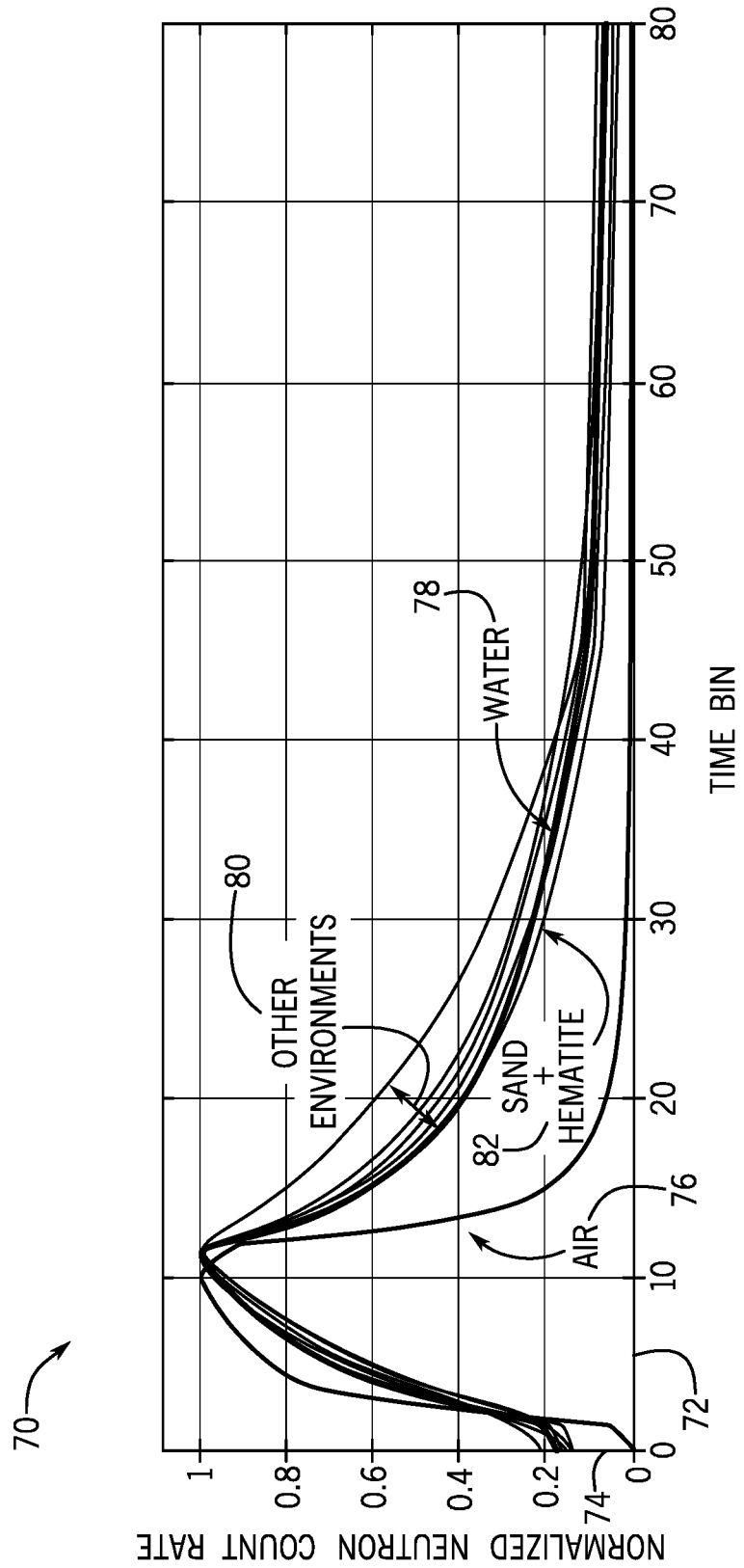
FIG. 4 is a plot of experimental neutron count rate time spectra, in accordance with an embodiment.

Depending on the environment of the downhole tool 12, the count rate of detected neutrons and neutron induced gamma rays may vary. FIG. 4 shows a graph 70 of the time spectrum of neutron count rates (i.e. the neutron count rate as a function of time with respect to a neutron burst start time) detected in multiple environments. The x-axis 72 displays time, and the y-axis 74 displays the detected neutron count rate for each time bin normalized to the maximum count rate of each environment. As depicted, the detected neutron count rate may rise to a maximum more quickly and die away more rapidly when the downhole tool 12 is in an air environment 76 than in a water environment 78, other environments 80, or a sand hematite matrix 82. The die away beginning in time bins 10 and 11 of the graph 70 may correspond to the end of a neutron burst 58 and beginning of an off period 60.

The density of atoms (e.g., hydrogen atoms) in an air environment is much lower than in the other environments found, for example, in a borehole 16 (even if the borehole 16 is filled with air) or laboratory setting (e.g., in a water-filled tank). Therefore, neutrons emitted from the neutron source 40, may scatter off of nuclei in air and return to the neutron detector 42 less often than in other environments. Therefore, the measured signal may be low and/or disappear rapidly. Additionally, a water environment 78 and a sand hematite matrix 82 may represent non-air environments that also have relatively quick neutron die away compared to other environments. This may be due to the relatively high probability for neutron capture by the elements (e.g., hydrogen, iron, etc.) and the rapid slowing down and short range of the neutrons in the presence of such elements. Because of this, water may be used as a neutron shield, for example, in a laboratory setting. As such, the water environment 78 and sand hematite matrix 82 may be considered as reference environments indicative of non-air environments, but have characteristic graphs closer to the graph of the air environment 76 than other environments 80. As such, the water environment 78 may be used to illustrate the differences between the air environment 76 and the non-air environments.

Figure 5:
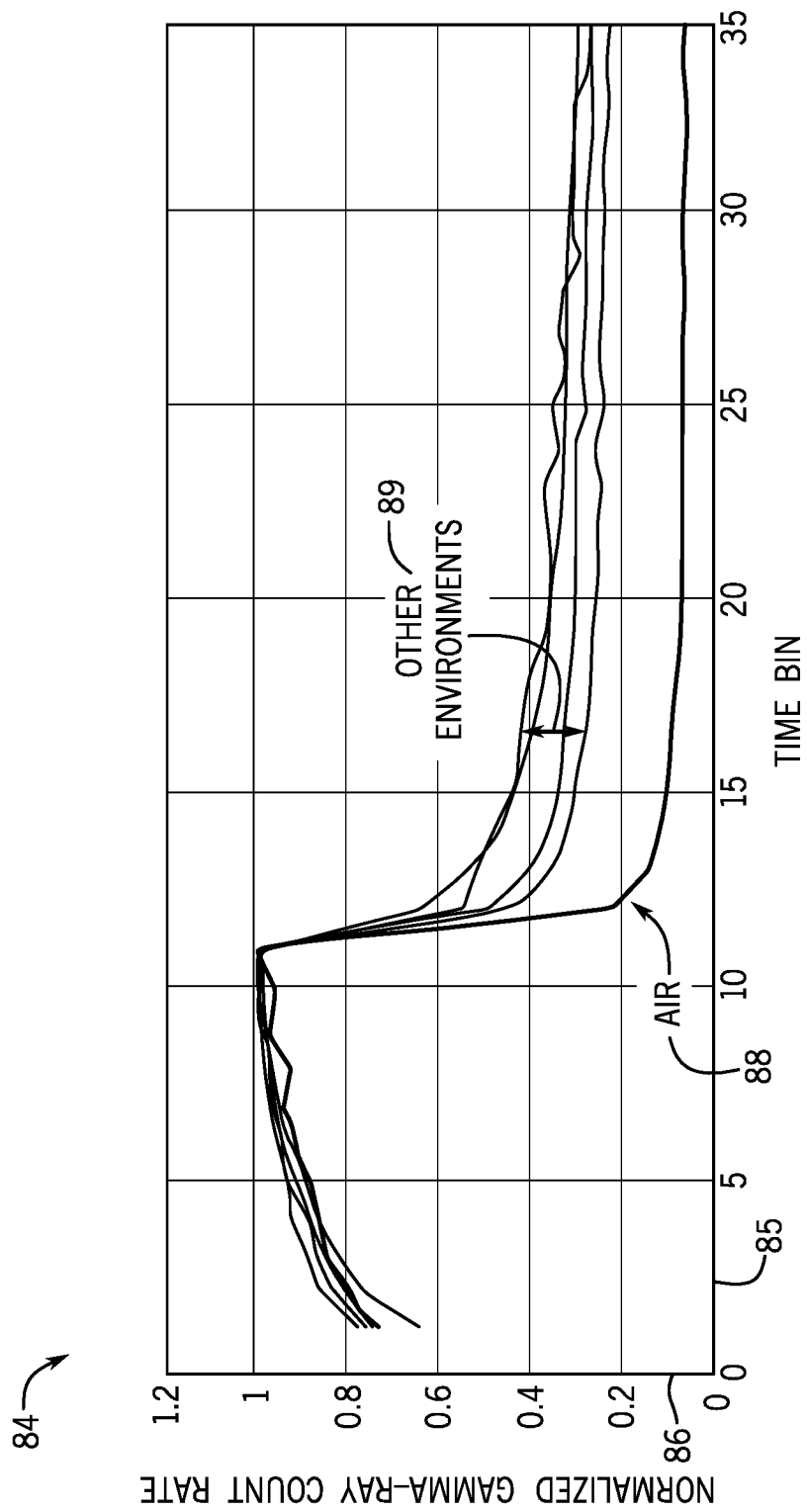
FIG. 5 is a plot of gamma-ray count rate time spectra, in accordance with an embodiment.

Similarly, gamma-ray spectra (e.g., time, energy, etc.) may also exhibit notable characteristics with regard to the environment as shown by graph 84 of FIG. 5 illustrating a gamma-ray time spectrum with time on the x-axis 85 and the normalized gamma-ray count rate on the y-axis 86. As neutron induced gamma rays are generated by inelastic scattering reactions or capture of the neutrons, the gamma-ray count rate may follow that of the neutrons. As such, the gamma-ray count rate may be relatively high during a neutron burst 58 and die away quickly after off period 60 has begun. Additionally, the die away of the gamma-ray count rate in an air environment 88 may occur faster than in other environments 89. As stated above, gamma rays are induced by both inelastic scattering and neutron capture. The gamma rays from inelastic scattering may dominate the signal during a neutron burst 58, and gamma rays from neutron capture may dominate the signal during the off period 60. As stated above in regard to graph 70 of neutrons, non-air environments may have a higher density and, thus, have more neutron capture events and, thus, produce more capture gamma rays. Although the capture gamma-ray signal may distinguish the air environment 88 from other environments 89, the inelastic scattering gamma-ray signal may also be used.

Figure 6:
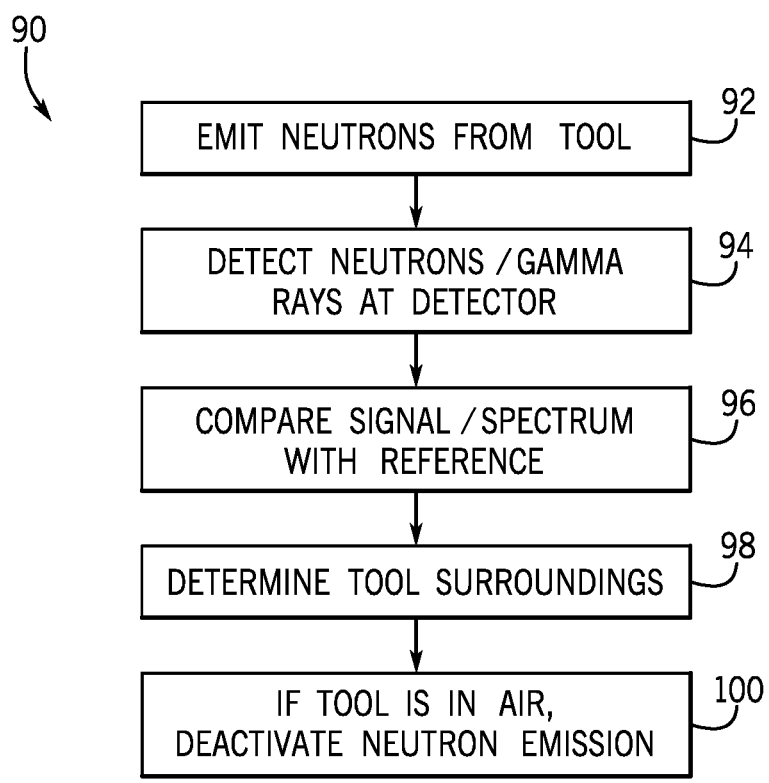
FIG. 6 is a flowchart for deactivating a neutron source, in accordance with an embodiment.

Based on the differences between the air environment 76/88 and the non-air environments (e.g., the water environment 78) with respect to the time spectrum of neutron or neutron induced gamma-ray count rates, the downhole tool 12 may detect if it is in an air environment 76. FIG. 6 illustrates a flowchart 90 of a process to determine if a downhole tool 12 is emitting neutrons in air, and, if it is, to deactivate neutron emission. Neutrons may be emitted from a downhole tool 12 using a neutron source 40 (process block 92). The neutrons and/or gamma rays may also be detected at one or more neutron or gamma ray detectors 42 (process block 94). A data processing system 28 may take the total counts, count rates, and/or energy levels of the detected neutrons or gamma rays and compare the measured signal/spectrum to corresponding characteristics of a reference signal, spectrum, and/or value (process block 96). For example, the data processing system 28 may take the measured count rate of neutrons or gamma rays and compare it to a reference count rate of a non-air environment such as water or sand hematite in a time spectrum. Additionally or alternatively, the time spectrum of count rates may be gathered from a single neutron pulse 56 or gathered (e.g., averaged) over multiple pulses 56 or packets 54. Additionally, the time spectrum may be compared to one or more reference spectra. From the comparison, the data processing system 28 may determine the surroundings of the downhole tool 12 (process block 98). This determination may also be made using one or more comparisons over one or more neutron pulses 56 or packets 54. Additionally, if the downhole tool 12 is determined to be in air, the data processing system 28 may deactivate neutron emission (process block 100) and/or issue a warning. Although the flowchart 90 is shown in a given order, in certain embodiments, portions of the flowchart may be reordered, deleted, occur simultaneously, and/or be initiated and/or controlled by multiple data processing systems 28.

Figure 7:
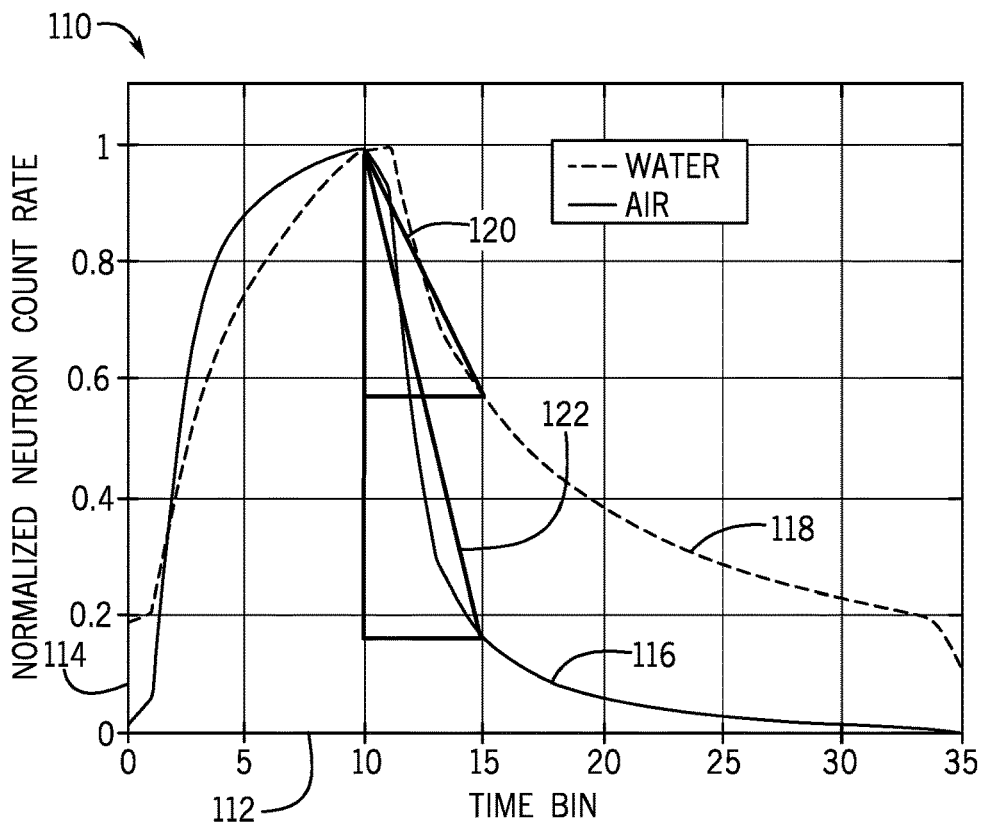
FIG. 7 is a plot of experimental neutron count rate time spectra and associated slopes, in accordance with an embodiment.

In one embodiment, the time spectrum of detected neutrons may be analyzed using the slope of the normalized neutron count rates, as illustrated by graph 110 of FIG. 7. The x-axis 112 displays time, and the y-axis 114 displays the detected neutron count rate normalized to the maximum of each environment (i.e., air environment 116 and water environment 118). For example, the water slope 120 between time bins 10 and 15 may not be as steep as the air slope 122 in the same region. The increased gradient of the air slope 122 may indicate a more rapid neutron die away during an off period 60 of the neutron source 40. This rapid die away may occur in part because there are fewer nuclei (e.g., hydrogen nuclei) in air for the emitted neutrons to be thermalized by (i.e. lose their energy to) and/or bounce back from and be detected by detector 42, whereas a non-air environment may have a higher density of atoms, and, therefore, may have more nuclei to scatter and/or thermalize the neutrons. This increased scattering of neutrons may cause more neutrons to return to the detector 42 and do so over a longer period of time. As such, if the downhole tool 12 measured neutron die away with a gradient steeper than a threshold value (e.g. a reference value based at least in part on a non-air environment slope) the downhole tool 12 may determine if it is in air. Such a threshold value may be obtained experimentally. Additionally, the slope may be calculated by a moments method (e.g., moment-area method), linear interpolation, a first derivative method, or any other suitable method for finding or estimating the slope of the neutron die away. As such an average or instantaneous slope may be used.

Likewise, the slope of the increasing neutron count rate in the time spectrum may be used to differentiate between an air environment 116 and non-air environment. For example, the slope between time bins 4 and 10 may be greater in a non-air environment (e.g., water environment 118) than an air environment 116. Additionally, the increasing slope may correspond to a time bin during a neutron burst 58. The regions (e.g., time bins) in which the slope(s) are calculated may be shortened, lengthened, or shifted depending on the application.

Figure 8:
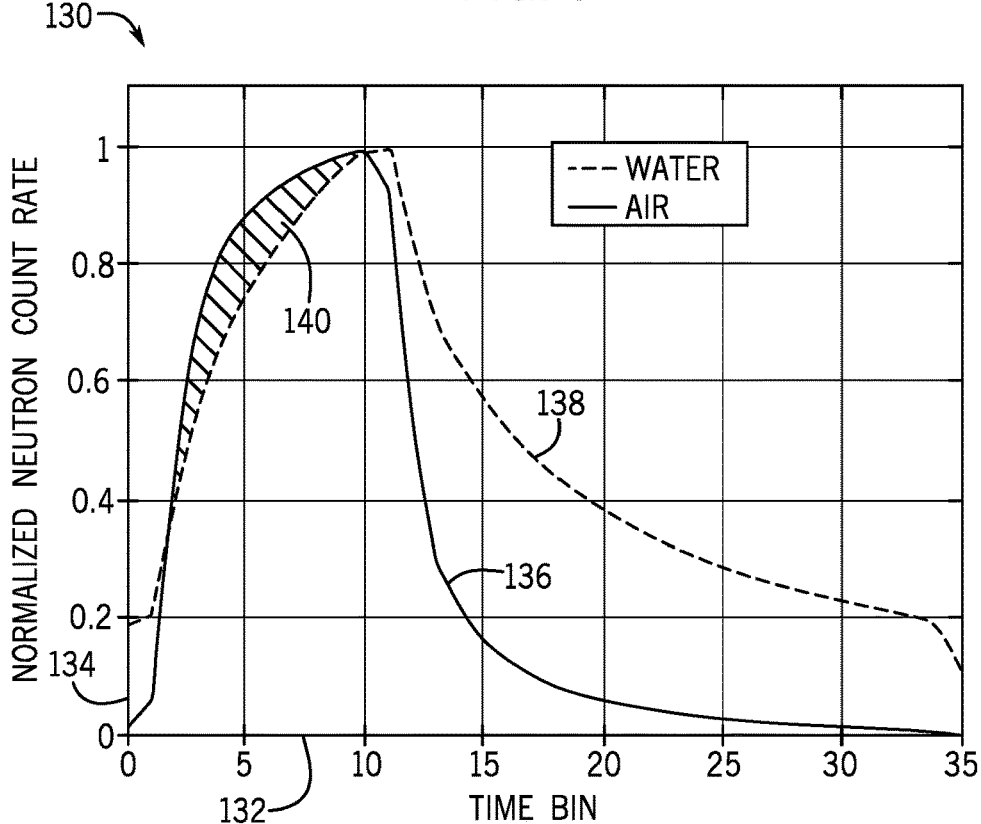
FIG. 8 is a plot of experimental neutron count rate time spectra and an associated area, in accordance with an embodiment.

In addition to the slopes of the neutron count rates, the areas between and/or under the normalized neutron count rates may be used to determine the downhole tool 12 environment, as shown by graph 130 in FIG. 8. The x-axis 132 displays time, and the y-axis 134 displays the detected neutron count rate normalized to the maximum of each environment (i.e., air environment 136 and water environment 138). In one embodiment, the area 140 between a reference environment (e.g., water environment 138) and measured environment (e.g., air environment 140) taken between time bins 1 and 10 may be greater than a threshold value. Additionally or alternatively, the total area under the measured curve may be used in comparison to a threshold value, as the area may correspond to a total count over a specified time period. The area may be calculated by a Riemann sum, integral, or any method suitable for area calculation or approximation. The regions (e.g., time bins) in which the areas are calculated may be shortened, lengthened, or shifted depending on the application, and may be during the neutron burst 58 and/or during an off period 60.

Figure 9:
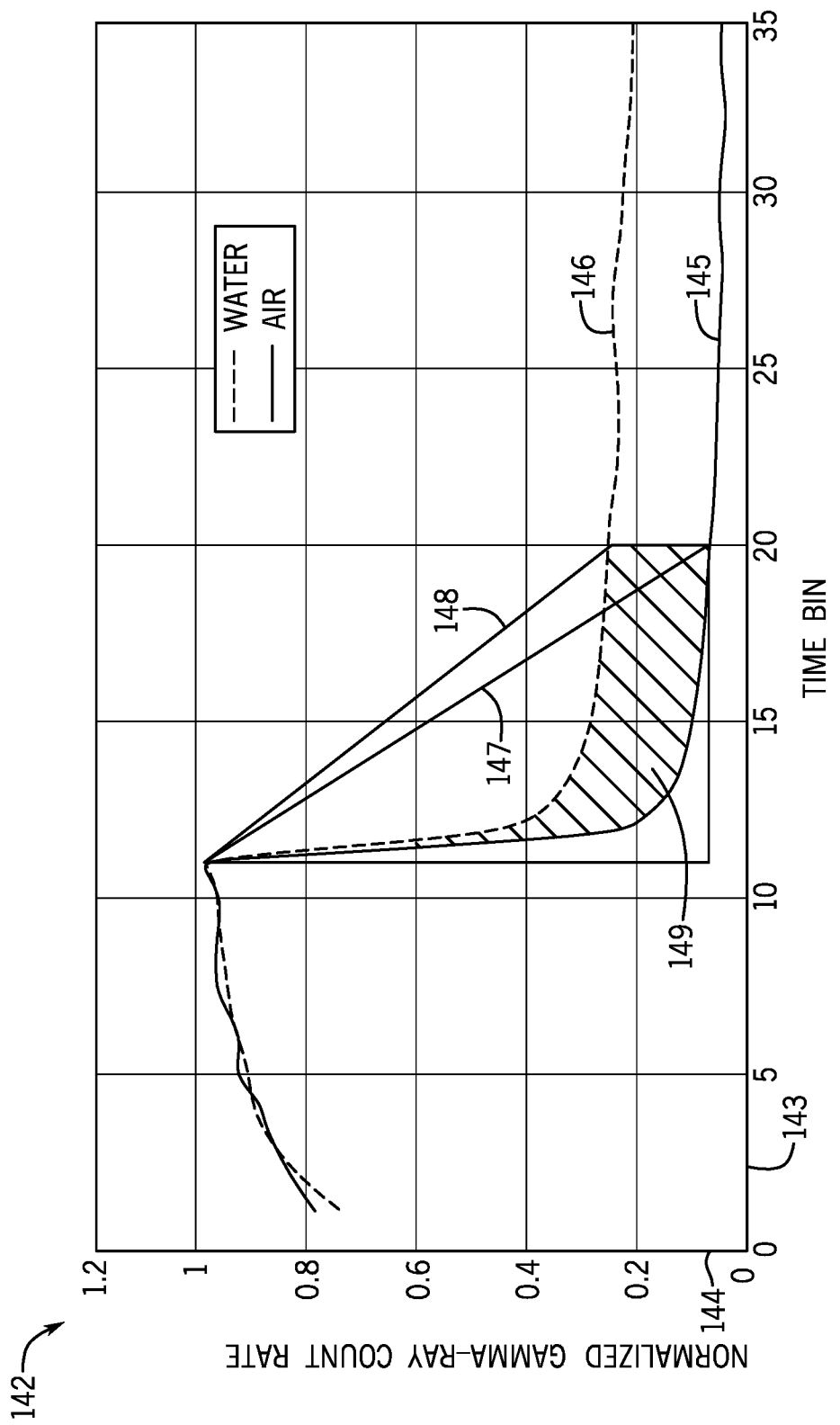
FIG. 9 is a plot of gamma-ray count rate time spectra and associated slopes and area, in accordance with an embodiment.

As stated above, gamma-ray measurements may also be used in a similar manner, as shown by graph 142 in FIG. 9. The x-axis 143 displays time, and the y-axis 144 displays the detected gamma-ray count rate normalized to the maximum of each environment (i.e., air environment 145 and water environment 146). The increased die away of gamma rays in the air environment may lead to a steeper air slope 147 than a water slope 148. As with the neutrons, this may be due to increased density and/or neutron capture in non-air environments (e.g., water environment 146). Additionally, the area 149 under or between the count rates of the air environment 145 and water environment 146 may be used and compared to a reference signal/value. Such slopes and/or areas may be calculated during and/or after the neutron burst 58, although the signal characteristics may be more visible during the off period 60. This discernibility may be due to the dominance of the capture gamma-ray signal.

Figure 10:
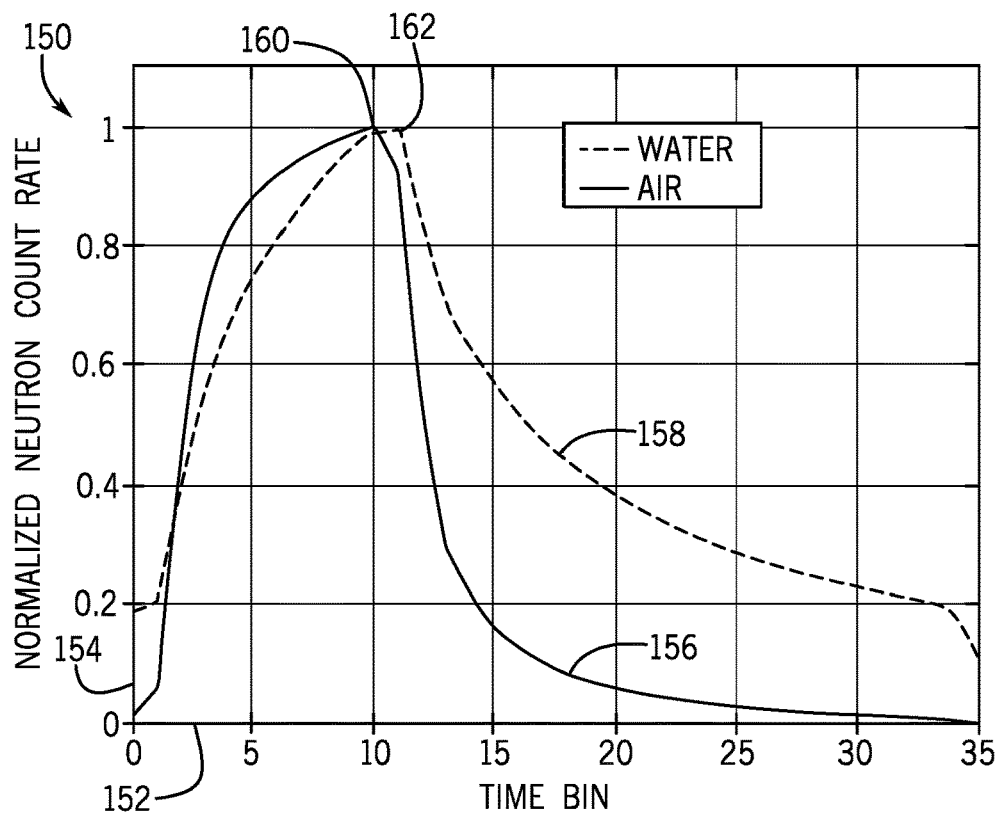
FIG. 10 is a plot of experimental neutron count rate time spectra and associated peaks, in accordance with an embodiment.

In another embodiment, the measured peak position in time of the normalized neutron count rate may be used to determine the environment surrounding the downhole tool 12, as shown by graph 150 of FIG. 10. The x-axis 152 displays time, and the y-axis 154 displays the detected neutron count rate normalized to the maximum of each environment (i.e., air environment 156 and water environment 158). As stated above, a non-air environment may have a higher density (e.g., more hydrogen atoms), and, therefore, may have more nuclei to scatter and thermalize the neutrons and cause more neutrons to return to the neutron detector with, however, a delayed return. As such, the air peak 160 may occur before (i.e., in a time bin prior to) a water peak 162. Additionally, air may have fewer nuclei to scatter and thermalize the emitted neutrons. An air environment may be determined by comparing a measured peak time of the normalized neutron count rate to a threshold time. This may also be used when comparing gamma-ray signals to reference signals. The increased likelihood of thermalized neutrons in a non-air environment may lead to an increase in neutron capture and, thus, an increase in capture gamma rays. This effect may materialize as a shifted peak in the air environment 156 and/or an earlier die away of the gamma-ray count rate. The regions (e.g., time bins) in which the peaks are calculated may be shortened, lengthened, or shifted depending on the application.

Neutron leakage from the neutron source 40 around/through the shield 44 may also be present and detected by the detector 42. This may contribute to the air peak 160 occurring first and dropping off rapidly thereafter. For example, once the neutron source 40 is in an off period 60, the neutron count rate may decrease rapidly, as few neutrons may return from the sparse air environment. Neutron leakage may be present independent of the environment, and may be a property of a particular downhole tool 12. However, the neutron leakage may be generally more prevalent at high energies (e.g., above 10 keV), as shown by graph 170 of FIG. 11.

Graph 170 illustrates a modeled normalized neutron count 174 vs. the neutron energy levels 172 on a logarithmic scale. The neutron count 174 is normalized by the total neutrons emitted, or an approximation thereof, which may be obtained, in operation, using a neutron monitor 46. As mentioned above, because of the density and prolificacy of nuclei and the possible presence of hydrogen in non-air environments, the air environment 176 may have fewer total neutron counts 174 than a non-air environment (e.g., water environment 178). At low energy levels, for example less than 10 keV, the difference in neutron counts 174 may become more noticeable, as shown by the ratio 180 of the water environment 178 to the air environment 176. At energy levels near that of thermal and/or epithermal neutrons the neutron counts 174 may be, for example, 6 times greater in a non-air environment than in an air environment 176. As such, thermal and/or epithermal neutrons may be used in making the time spectrum from which slopes, areas, and peaks may be determined and compared to threshold values/spectra, although other energy regions that show a sensitivity to the environment may be used as well.

Additionally, the measured neutron count 174 may be used in determining the environment of a downhole tool 12. As described above, graph 170 shows that the air environment 176 has fewer neutron counts 174 than the non-air environment in the lower energy range. Therefore, if the measured neutron count 174 is below a threshold value, the downhole tool 12 may be determined to be in an air environment. However, the neutron counts 174 may be proportional to the neutron output of the neutron source 40. Additionally, the number of emitted neutrons from the neutron source 40 may be affected by operating conditions of the neutron source 40 such as temperature, gas pressure, and/or target erosion (aging) and may, therefore, vary from one test to another. To compensate for this, a neutron monitor 46, located near the neutron source 40, may detect the neutron flux emitted from the neutron source 40. This neutron flux may be used as a reference and/or means of normalization to determine if a measured neutron count 176 is above or below a threshold value, and therefore determine the environment of the downhole tool 12.

Using a neutron monitor 46 and a detector 42 to determine the neutron count 174 and a threshold value may rely on the proper function of both detectors. However, when gathering a time spectrum of the count rate (e.g., graph 70) for analysis a single detector 42 may be used. The reliance on a single detector 42 may yield results with less error, or may be less susceptible to detector failure. Additionally, the use of the time spectrum and at least one detector may generate a characteristic measurement independent of the neutron flux. However, multiple detectors 42 may also be used to gather time spectra to duplicate and/or perform other analyses in order to obtain a more accurate determination of the environment of the downhole tool 12.

Figure 11:
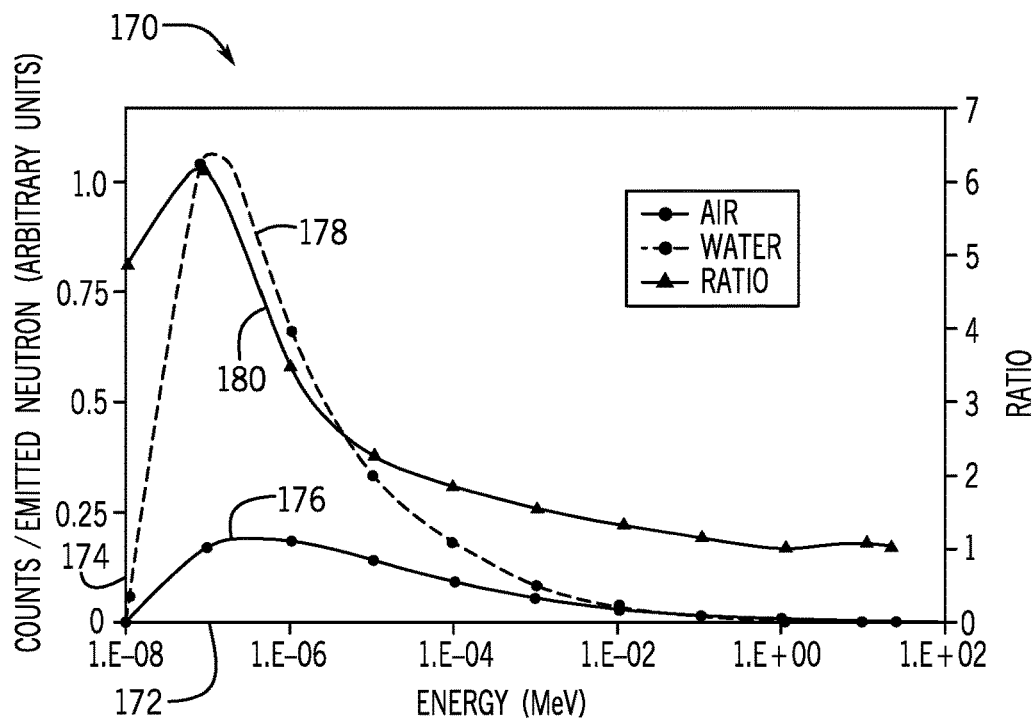
FIG. 11 is a plot of modeled total neutron counts at associated energies, in accordance with an embodiment.

As indicated in the graph 170 of FIG. 11, the average energy of neutrons reaching the neutron detector 42 may be higher if the downhole tool 12 finds itself in air or a similar environment. In one embodiment, the ratio of neutrons at different energy levels 172 may be used to determine the environment. For example, if the ratio of thermal neutrons (i.e., generally about 0.025 eV at room temperature) and epithermal neutrons (i.e., generally about or above 0.4 eV) is low (e.g., less than 1 or a threshold value) the downhole tool 12 may be in an air environment. Additionally, the measurement of the thermal and epithermal neutrons may be done by separate detectors 42, and the detectors 42 may be placed at equal or different distances from the neutron source 40.

Figure 12:
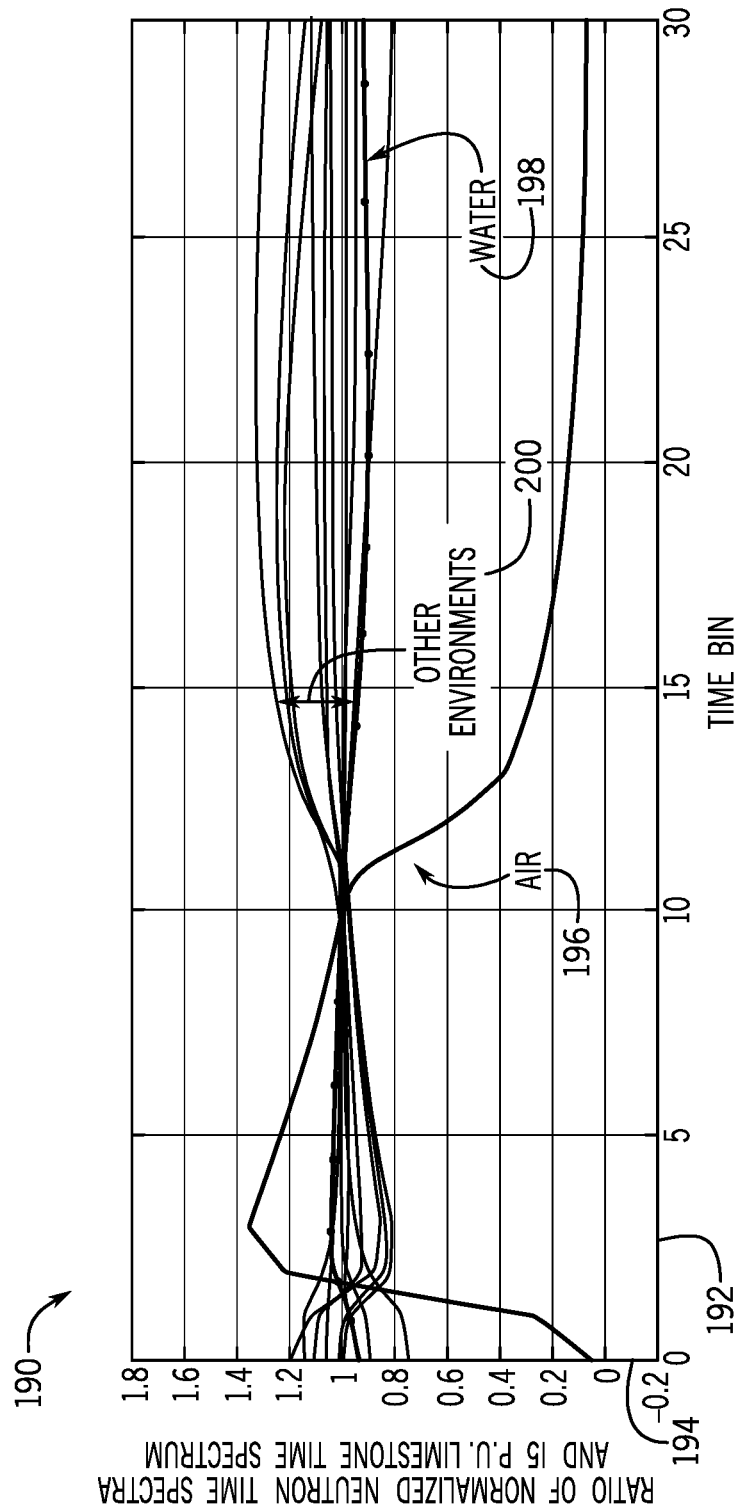
FIG. 12 is a plot of experimental neutron count rate time spectra normalized to a 15-p.u. limestone fresh water reference spectrum, in accordance with an embodiment.

Although the time spectrum of FIG. 4 is normalized to the maximum count rates of each environment, other normalizations may be used to observe the differences in the time spectrum when the downhole tool 12 is in air. For example, the graph 190 of FIG. 12 shows time on the x-axis 192 and neutron count rates normalized to their maximum divided by the normalized 15-percentage unit (p.u.) limestone time spectrum obtained with a borehole filled with freshwater on the y-axis 194. A 15-p.u. limestone borehole filled with freshwater may be a general example of a borehole environment. As shown, the air environment 196 displays noticeable differences from the water environment 198 and other environments 200 (i.e., non-air environments). As described above, thresholds, slopes, areas, peaks, and other characteristics of the graph 190 may be used to determine if the downhole tool 12 is in an air environment 196. Additionally, the time spectrum may be normalized to the air environment, water environment, or any other environment suitable for displaying features for determining if the downhole tool 12 is in air.

Figure 13:
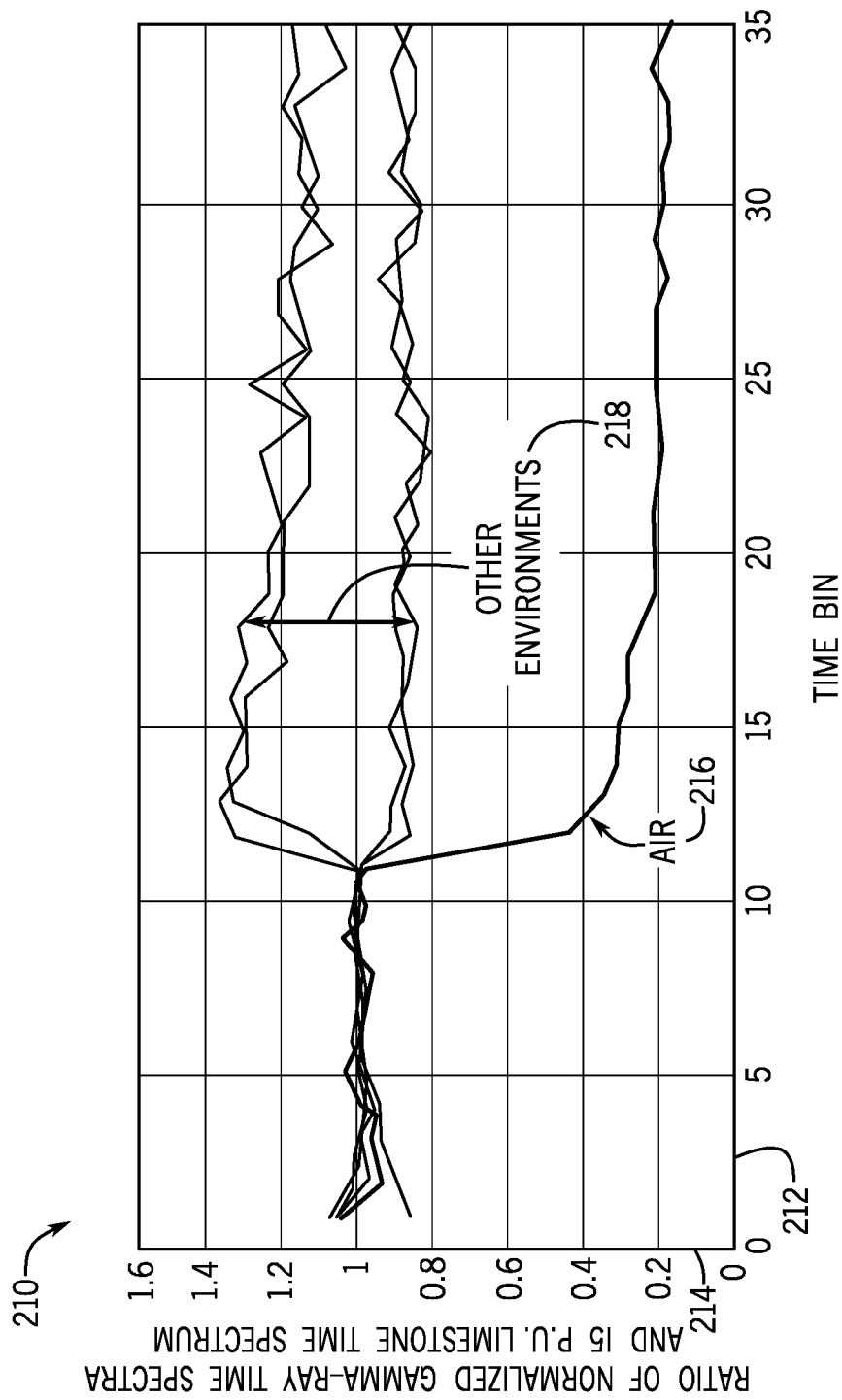
FIG. 13 is a plot of gamma-ray count rate time spectra normalized to a 15-p.u. limestone fresh water reference spectrum, in accordance with an embodiment.

Similarly, the gamma-ray signal may be normalized by a reference signal before being analyzed, as shown by graph 210 in FIG. 13 where time is displayed on the x-axis 212 and gamma-ray count rates normalized to their maximum divided by the normalized 15-p.u. limestone time spectrum obtained with a borehole filled with freshwater on the y-axis 214. As stated above, a 15-p.u. limestone borehole filled with freshwater may be a general example of a borehole environment, and, thus, may assist in displaying characteristics of the gamma-ray signal corresponding to an air environment 216. As illustrated, the air environment 216 may have a much lower normalized count rate than that of the other environments 218 after the neutron burst 58. This characteristic may allow the distinction between the air environment 216 and other environments 218.

In some embodiments, the downhole tool 12 may provide azimuthal measurements. For example, the downhole tool 12 may produce neutron emissions and/or have gamma-ray and/or neutron detectors 42 situated towards one or more directions. The azimuthal measurements may provide additional information about the environment, for example, when taking measurements in a borehole 16. In such embodiments, the measurements of each detector 42 may be analyzed collectively or individually. For example, while the measurements of the detectors 42 may be averaged or combined to create a single time spectrum and/or cumulative count, the measurements may also be used separately to detect if any of the measured directions are towards an air environment. In this manner, the neutron generator 40 may be deactivated if at least one detector 42 detects an environment of air.

Additionally, the methods of the present disclosure may be utilized to determine an environment of air or other environment that possess distinctions in a time or energy spectrum from that of the generally desired environments of a downhole tool 12 (e.g., borehole 16, laboratory setting, etc.). These distinctions may be evaluated based on a threshold value or a statistical analysis (e.g., a $\chi^2$ test) of the measured spectrum versus a reference spectrum or value. Additionally, multiple distinctions of the time and/or energy spectra may be analyzed simultaneously to provide a more accurate measurement of the surrounding environment. For example, a combination of high-energy gamma-ray counts, the slope, area, and/or peak of a count rate time spectrum, and/or the cumulative counts (e.g., normalized to the neutron flux) may be analyzed and considered together to determine if the downhole tool 12 is in an unfavorable environment for neutron emission. Furthermore, multiple variations of the neutron and/or gamma-ray signals may be used when comparing to a reference signal. For example, instead of analyzing the graph 170 of neutron counts 174 vs. energy level 172, the slope (e.g., derivative) of the neutron counts 174, the count rates at corresponding energy levels, may also be used. As stated above, it may be undesirable to emit neutron radiation into an environment. As such, in environments such as air, or other environments where neutron emission may not be warranted/desired, the neutron source 40 may be shut down.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

The invention claimed is:

1. A system comprising:
   a pulsed neutron generator configured to emit neutrons in an environment;
   a radiation detector configured to take measurements of the neutrons; and data processing circuitry configured to determine if the environment surrounding the pulsed neutron generator is an air environment, based at least in part on a neutron signal obtained by the radiation detector, wherein the determination comprises comparing one or more characteristics of the neutron signal with one or more corresponding reference characteristics, wherein the data processing circuitry is configured to deactivate the pulsed neutron generator in response to determining that the pulsed neutron generator is in the air environment.

2. The system of claim 1, wherein the radiation detector is a neutron detector configured to detect thermal or epithermal neutrons.

3. The system of claim 1, wherein the one or more corresponding reference characteristics are indicative of a reference environment.

4. The system of claim 1, wherein the neutron signal is normalized to both the spectrum maximum and a reference time spectrum or a neutron emission count based at least in part on detections of a neutron monitor.

5. The system of claim 1, wherein the neutron signal comprises a time spectrum.

6. The system of claim 5, wherein the one or more characteristics of the neutron signal comprises a slope of a neutron count rate over the time spectrum.

7. The system of claim 6, wherein the slope corresponds to the time spectrum of the neutron count rate during a neutron burst of the pulsed neutron generator.

8. The system of claim 5, wherein the one or more characteristics of the neutron signal comprises an area defined at least in part by a curve of the time spectrum.

9. The system of claim 8, wherein the area comprises an area under the curve of the time spectrum or an area between the curve of the time spectrum and a reference curve.

10. The system of claim 8, wherein the area corresponds to the time spectrum during a neutron burst of the pulsed neutron generator.

11. The system of claim 5, wherein the one or more characteristics of the neutron signal comprises a peak in the time spectrum.

12. The system of claim 5, wherein the one or more characteristics are independent of a neutron flux of the neutron generator.

13. The system of claim 1, wherein the one or more reference characteristics are threshold values.

14. The system of claim 1, wherein the neutron signal comprises a ratio of a thermal neutron count and an epithermal neutron count.

15. A system comprising:
  a pulsed neutron generator configured to emit neutrons in an environment;
  a radiation detector configured to take measurements of the neutrons or neutron induced gamma rays; and
  data processing circuitry configured to determine if the environment surrounding the pulsed neutron generator is an air environment, based at least in part on a time spectrum, wherein the time spectrum comprises a neutron or gamma ray count rate based at least in part on the measurements of the neutrons or gamma rays and to deactivate the pulsed neutron generator in response to determining that the pulsed neutron generator is in the air environment.

16. The system of claim 15, wherein the radiation detector is configured to detect neutrons and gamma rays.

17. A method for deactivating a neutron generator in an undesired environment comprising:
  emitting neutrons, from the neutron generator, into an environment;
  detecting the neutrons or neutron induced gamma rays using one or more detectors;
  determining, via a processor, from the detected neutrons or gamma rays a time spectrum;
  determining, via the processor, if the environment is undesirable based at least in part on one or more characteristics of the time spectrum; and
  in response to determining that the environment is undesirable, disabling, via the processor, the neutron generator.

18. The method of claim 17, wherein the undesired environment is air.

19. The method of claim 17, comprising evaluating a difference between the one or more characteristics and one or more reference characteristics using a statistical analysis.

* * * * *